(12) United States Patent
Steiner et al.

(10) Patent No.: US 9,167,973 B2
(45) Date of Patent: Oct. 27, 2015

(54) PORTABLE SENSOR DEVICE AND PATIENT MONITOR

(75) Inventors: Christian Steiner, Munich (DE); Dominik Gutzler, Nuremberg (DE); Marcus Veeck, Koblenz (DE); Joerg Scheier, Munich (DE); Christoph Manegold, Munich (DE)

(73) Assignee: PULSION Medical Systems SE, Feldkirchen (DE)

(*) Notice: Subject to any disclaimer, the term of this patent is extended or adjusted under 35 U.S.C. 154(b) by 348 days.

(21) Appl. No.: 12/932,720

(22) Filed: Mar. 4, 2011

(65) Prior Publication Data

US 2011/0224531 A1     Sep. 15, 2011

(30) Foreign Application Priority Data

Mar. 8, 2010 (DE) .......................... 10 2010 010 610

(51) Int. Cl.
| | |
|---|---|
| A61B 5/021 | (2006.01) |
| A61B 5/023 | (2006.01) |
| A61B 8/04 | (2006.01) |
| A61B 5/0215 | (2006.01) |

(52) U.S. Cl.
CPC .............. *A61B 5/021* (2013.01); *A61B 5/02141* (2013.01); *A61B 5/023* (2013.01); *A61B 5/02156* (2013.01); *A61B 5/02158* (2013.01); *A61B 8/04* (2013.01); *A61B 2560/0431* (2013.01); *A61B 2560/0456* (2013.01)

(58) Field of Classification Search
USPC ........................................................ 600/407
See application file for complete search history.

(56) References Cited

U.S. PATENT DOCUMENTS

| | | | |
|---|---|---|---|
| 4,499,903 | A | 2/1985 | Furst et al. |
| 5,417,222 | A | 5/1995 | Dempsey et al. |
| 5,640,953 | A | 6/1997 | Bishop et al. |
| 5,711,302 | A * | 1/1998 | Lampropoulos et al. ..... 600/485 |

(Continued)

FOREIGN PATENT DOCUMENTS

| | | |
|---|---|---|
| CN | 1330525 A | 1/2002 |
| CN | 101536941 A | 9/2009 |

(Continued)

OTHER PUBLICATIONS

The Basics of Packaging by Case Medical pub. online Jun. 8, 2006, http://www.casemed.com/caseacademy/downloads/CASDF002.pdf.*

(Continued)

*Primary Examiner* — Katherine Fernandez
*Assistant Examiner* — Michael Kellogg
(74) *Attorney, Agent, or Firm* — Collard & Roe, P.C.

(57) ABSTRACT

The portable sensor device is connected with the arterial pressure measurement catheter by way of a pressure hose. The electronic pressure sensor is accommodated in the sensor housing. The analog sensor signal is output to the patient monitor by way of a cable. Aside from the channel for the analog sensor signal, additional channels are provided for communication between sensor device and patient monitor. A bidirectional channel serves for writing to and querying the memory module, in which patient data, such as age, gender, height/weight, etc., can be stored. The three-way cock possesses the settings "M" (measurement operation) and "0" (calibration measurement), in which the contactor is brought into connection with the contact. The switching contact is transmitted to the patient monitor, which thereby automatically recognizes zeroing of the sensor.

9 Claims, 2 Drawing Sheets

(56) References Cited

U.S. PATENT DOCUMENTS

| | | | |
|---|---|---|---|
| 5,758,657 A | 6/1998 | MacEachern | |
| 6,159,147 A | 12/2000 | Lichter et al. | |
| 6,394,961 B1 | 5/2002 | Pfeiffer et al. | |
| 6,585,660 B2 | 7/2003 | Dorando et al. | |
| 6,659,754 B1 * | 12/2003 | Smith | 425/174.8 E |
| 7,314,449 B2 | 1/2008 | Pfeiffer et al. | |
| 7,588,542 B2 | 9/2009 | Pfeiffer et al. | |
| 7,666,146 B2 | 2/2010 | Pfeiffer et al. | |
| 7,850,617 B2 | 12/2010 | Goedje et al. | |
| 7,946,997 B2 | 5/2011 | Huebinette | |
| 8,932,217 B2 | 1/2015 | Gibson et al. | |
| 2004/0249297 A1 | 12/2004 | Pfeiffer et al. | |
| 2005/0267378 A1 | 12/2005 | Pfeiffer et al. | |
| 2005/0267379 A1 | 12/2005 | Pfeiffer et al. | |
| 2007/0084990 A1 * | 4/2007 | Coates | 250/226 |
| 2007/0179400 A1 * | 8/2007 | Dijkman | 600/561 |
| 2007/0287929 A1 | 12/2007 | Goedje et al. | |
| 2008/0255440 A1 | 10/2008 | Eilersen et al. | |
| 2008/0281168 A1 | 11/2008 | Gibson et al. | |
| 2009/0192541 A1 | 7/2009 | Ortiz et al. | |

FOREIGN PATENT DOCUMENTS

| | | |
|---|---|---|
| DE | 94 08 557 | 7/1994 |
| DE | 10 2005 032 431 | 9/2006 |
| EP | 0 814 699 B1 | 1/1998 |
| JP | H07-213494 A | 8/1995 |
| JP | H08-103416 A | 4/1996 |
| JP | H08-504345 A | 5/1996 |
| JP | H08-280635 A | 10/1996 |
| JP | H10-208182 A | 8/1998 |
| JP | 2003-512120 A | 4/2003 |
| JP | 2004-202250 A | 7/2004 |
| JP | 2004-528920 A | 9/2004 |
| JP | 2005-305173 A | 11/2005 |
| JP | 2005-329237 A | 12/2005 |
| JP | 2007-283109 A | 11/2007 |
| JP | 2008-508971 A | 3/2008 |
| JP | 2008-526443 A | 7/2008 |
| JP | 2010-518900 A | 6/2010 |
| WO | 94/13198 A1 | 6/1994 |
| WO | 00/21434 A1 | 4/2000 |
| WO | 01/30237 A1 | 5/2001 |
| WO | 02/094339 A2 | 11/2002 |
| WO | 2006/015922 A1 | 2/2006 |
| WO | 2006/076498 A2 | 7/2006 |
| WO | 2008/100208 A1 | 8/2008 |

OTHER PUBLICATIONS

European Search Report dated Nov. 16, 2011 in European Application No. EP 11 15 6534 with English translation.
"PiCCO plus setup" PULSION Medical Systems, 1. Apr. 2007, www.pulsion.de/fileadmin/Pulsion-share/Products/PiCCO/US/Piccoplus-ShortSetup_US_MPI812905US_ROO_190407.pdf (European SR).
"PiCCO2 Advanced Hemodynamic Monitoring," PULSION Medical Systems, 2008, total of 44 pages.

* cited by examiner

PORTABLE SENSOR DEVICE AND PATIENT MONITOR

CROSS REFERENCE TO RELATED APPLICATIONS

Applicants claim priority under 35 U.S.C. 119 of German Application No. 10 2010 010 610.0 filed Mar. 8, 2010, the disclosure of which is incorporated by reference.

BACKGROUND OF THE INVENTION

The present invention relates to a portable sensor device, particularly a portable sensor device that comprises an electronic sensor component for measuring a physiological variable at a measurement site of the body of a patient, a measurement site interface for connecting the electronic sensor component to measurement site connection means for establishing a measurement connection between the electronic sensor component and the measurement site, a patient monitor interface for connecting the electronic sensor component to patient monitor connection means for establishing a signal connection between the electronic sensor component and the patient monitor, and a sensor housing for accommodating the electronic sensor component, the measurement site interface, and the patient monitor interface.

Furthermore, the invention relates to a patient monitor, particularly a patient monitor that comprises a sensor interface for connecting patient monitor connection means in order to establish a signal connection between a portable sensor device, of the type stated initially, and the patient monitor.

Such portable sensor devices and related patient monitors are known in many forms from clinical use. In particular, patient monitors that monitor a pressure measured in an intravascular manner, by means of an arterial catheter, have been widespread for a long time. In this connection, the fluid pressure at the measurement site is transferred, by way of a pressure hose, to a portable sensor device that essentially consists of an electronic pressure sensor encased in a housing, as well as a plug for outputting the sensor signal to the patient monitor by way of a suitable cable.

Corresponding sensor devices and patient monitors are commercially available as "PiCCO technology" from the patent applicant PULSION Medical Systems AG, for example.

In the clinical use of portable sensor devices and related patient monitors of the type mentioned initially, problems can occur due to clinical personnel being put under additional stress as the result of having to enter, into the patient monitor, data that stand in connection with the use of the sensor device or are actually required for its use. These can be, for example, patient data, calibration data, sensor type data, etc. Such data entry requires time and attention of the clinical personnel, thus reducing correspondingly the time and attention available for the patient. The time expenditure required for data entry and the accompanying distraction might often be tolerable, but generally, they increase the likelihood of error; this is the more the case, the more frequently the data entries need to be performed.

Incorrect data entries can furthermore lead to incorrect diagnosis results, if physiological parameters are normalized with an incorrect patient weight, for example.

Frequently, a patient passes through several stages in a clinic, which stages require monitoring of physiological variables by means of patient monitors, for example emergency admission, preoperative stay in an intensive-care unit, surgical treatment in the operating room, and postoperative stay in an intensive-care unit. If entry of comprehensive data into the patient monitor in question is required anew every time, the above problem is further intensified.

SUMMARY OF THE INVENTION

In view of the above problems, it is an object of the present invention to make available a portable sensor device and a related patient monitor, which reduce the effort for data entries.

According to the invention, this object is achieved by providing an additional channel provided, along with the channel for transmission of the data signal, for transmission of data between sensor device and patient monitor. In this connection, not only embodiments that allow transmission of data that go beyond the mere sensor signal from the sensor device to the patient monitor, but also embodiments that allow the transmission of data from the patient monitor to the sensor device, can be advantageous. These two embodiments in combination can be particularly advantageous.

Data entries on the patient monitor often serve for the interplay of patient monitor and sensor device. This interplay can be improved, according to the invention, not only by means of transmission of data that go beyond the mere sensor signal (for example a sensor type identifier or a calibration value) from the sensor device to the patient monitor, but also by means of transmission of data from the patient monitor to the sensor device.

According to one aspect of the present invention, the underlying object is therefore accomplished by providing a portable sensor device of the type indicated mentioned, wherein the patient monitor interface comprises an input channel for receiving a data signal from the patient monitor, and the portable sensor device comprises at least one electronic additional component that can be influenced by the data signal.

The data signal is preferably a digital signal, but the invention can advantageously be implemented also with an analog data signal (for example a modulated signal).

According to another aspect of the present invention, the underlying object is achieved by providing a patient monitor that comprises a sensor interface for connecting the patient monitor connection means in order to establish a signal connection between a portable sensor device according to the invention and the patient monitor, wherein the sensor interface comprises a data output channel for output of a data signal, via the patient monitor connection means, to the portable sensor device.

Preferably, the at least one electronic additional component of sensor device is or includes a memory for storing patient data. In this way, patient data such as age, gender, height, or weight, as well as, if applicable, variables derived from them, such as body mass index, specific body surface area, etc., which have previously been entered into the patient monitor or calculated by the monitor, can be read out to the sensor device. If a patient passes through several stages in a clinic, for example emergency admission, preoperative stay in an intensive-care unit, surgical treatment in the operating room, and postoperative stay in an intensive-care unit, then the data do not have to be entered into the respective patient monitor anew every time. Instead, it is sufficient to enter the data into the first patient monitor that is used. The portable sensor device can then remain with the patient as a type of electronic patient ID (for example on a holder at the patient's bedside, on an upper arm strap or chest strap of the patient, or the like), and can make the data available to every other patient monitor that is used. Patient data of the type stated are sometimes needed by patient monitors in order to be able to normalize, in suitable manner, physiological parameters that are determined, or in order to allow certain output that supports a diagnosis, i.e., for example, to issue an alarm if a parameter that is being determined assumes a critical value, or if a parameter that is being determined cannot be calculated reliably under the given circumstances. For example, completely different threshold values can apply for pediatric or geriatric patients, above (or below) which a specific hemodynamic parameter must be considered critical, or certain parameters only make diagnostic sense if they are normalized to the height, the weight, the body mass index, or the like.

While the special embodiment last described requires a channel for output of the stored data to other patient monitors, transmission of data from the patient monitor to the sensor device can reduce the stress on the clinical personnel even if no channel for output of data stored in the sensor device is provided. For example, as will be explained below, alarm functions that are dependent on patient data can be implemented in the sensor device instead of in the patient monitor. Or, instead, adaptation functions for correct communication between patient monitor and sensor device are implemented on the sensor side instead of on the monitor side (for example, a monitor-connection-specific adaptation of the output impedance of the sensor device instead of a sensor-connection-specific adaptation of the input impedance of the patient monitor connection in question).

According to an advantageous embodiment, the sensor device has an optical and/or acoustical output device. In advantageous manner, this can be one or more light-emitting diodes, a small liquid crystal display, an electronic sound chip with a respective loudspeaker, or the like, for example. Depending on how the sensor device is equipped electronically, such an output device can be controlled by corresponding components of the sensor device or by the patient monitor directly, by way of the input channel of the sensor device. In this way, different alarm functions can be implemented advantageously, for example a warning if a critical threshold value of a physiological parameter is not reached or is exceeded, in the event of communication problems between patient monitor and sensor device, or in the event of other technical problems, etc. Instead of or in addition to mere alarm functions, more complex display functions can be implemented advantageously, for example display of patient data on a liquid crystal display. Such output devices can be integrated into the sensor housing, but do not have to be, but rather can be accommodated on a plug-in additional module or the like, for example.

According to a particularly preferred embodiment of the invention, the electronic sensor component is configured for measurement of pressure and/or flux. Generally, sensor technology already known per se from the art can be provided for this purpose, i.e. capacitive membrane pressure transducers or piezo pressure transducers, for example.

Advantageously, the measurement site interface can be configured for connecting a pressure-transferring hose element for establishing a hydraulic connection between the measurement site and the electronic sensor component. Implementation as a Luer lock connector is possible, for example. Preferably, a pressure line interface is provided for connecting the portable sensor device to second sensor connection means for establishing a hydraulic connection between the pressure-transferring hose element and an additional sensor. In this way, two pressure sensors can be connected to a pressure line, i.e. the sensor device according to the invention can be connected between a conventional sensor device and a pressure measurement catheter, for example, so that two monitors (for example a patient monitor for determining hemodynamic parameters by means of pulse contour analysis and a simpler blood pressure monitor) can be operated at the same time, with a respective compatible sensor.

Preferably, the portable sensor device is smaller, in the direction of its greatest expanse, then 100 millimeters, and/or lighter than 100 grams, which is particularly advantageous if the sensor is supposed to remain on or with the patient over several departments, for example in order to allow the transfer of patient data to changing patient monitors, as described above. For being affixed to the patient's bedside, the sensor housing preferably has a mechanical holding connector that makes it possible to affix the sensor device to a holder at the patient's bedside, preferably without tools, and, also preferably without tools, to release it from this holder. According to a particularly advantageous embodiment, the holding connector can be combined with an adapter system that allows a connection to different holders, so that connectivity to different holder plate systems used in clinical practice, in particular, is guaranteed.

Preferably, the sensor device is sterile, so that it can also be used in the OP sector. For this purpose, the portable sensor device is advantageously kept in sterile packaging, before use.

According to a particularly preferred embodiment, the patient monitor interface is set up for establishing an analog signal connection between the electronic sensor component and the patient monitor for transmitting an analog sensor signal, the portable sensor device has an electronic identification component for making available an identification signal, which identifies a property of the sensor signal to be transmitted by the analog signal connection, and the patient monitor interface has a separate identification channel for output of the identification signal to the patient monitor.

In more general manner, i.e. independent of whether or not the patient monitor interface has an input channel for receiving a data signal from the patient monitor, according to one aspect of the invention, a portable sensor device is made available, which has the following. An electronic sensor component for measuring a physiological variable at a measurement site of the body of a patient, a measurement site interface for connecting the electronic sensor component to measurement site connection means for establishing a measurement connection between the electronic sensor component and the measurement site, a patient monitor interface for connecting the electronic sensor component to patient monitor connection means for establishing an analog signal connection between the electronic sensor component and the patient monitor for transmission of an analog signal, and a sensor housing for accommodating the electronic sensor component, the measurement site interface, and the patient monitor interface. Therein, the portable sensor device has an electronic identification component for making available an identification signal, which identifies a property of the sensor signal to be transmitted by the analog signal connection, and the patient monitor interface has a separate identification channel for output of the identification signal to the patient monitor.

In this way, calibration data stored in the sensor device, for example, can be transmitted to the patient monitor in order to allow a correct sensor signal evaluation. In this way, advantageously flexible connection systems can also be implemented, in which multiple and/or different sensors can be connected to a patient monitor, and the monitor recognizes how the respective signal is to be processed.

The identification signal is preferably a digital signal, but the invention can advantageously be implemented also with an analog identification signal (for example a modulated signal).

In the case of a corresponding advantageous patient monitor, the sensor interface for connecting patient monitor connection means is configured for establishing an analog signal connection between such a portable sensor device and the patient monitor, and the patient monitor has a separate recognition channel for reading the identification signal into the patient monitor. The patient monitor is adapted for processing the sensor signal to be transmitted by means of the analog signal connection depending on the identification signal.

For example, such a patient monitor can be provided with multiple sensor connectors, wherein it is unimportant which individual sensor connector is used for connecting a specific sensor device, because the patient monitor recognizes the corresponding identification signal, and correctly assigns and processes the sensor signal that comes in via the corresponding sensor connector.

According to a particularly advantageous further development of the invention, the identification component is equipped with zero recognition means for recognizing a zero adjustment, and the identification signal identifies the sensor signal as a zero signal. In advantageous manner, such a function for identifying the sensor signal as a zero signal can be combined with other identification signals for transmitting the sensor type, or the like.

The zero recognition means can be implemented in different ways. If the electronic sensor component of a sensor device according to the invention is configured as a pressure sensor, and if the sensor device comprises a valve device that can be operated manually (for example a three-way cock) for zeroing with atmospheric pressure, then the valve device can be provided with a switch contact that recognizes a valve setting in which a connection to the atmosphere is established. Alternatively, a micro-controller, DSP, or the like can be provided in the sensor device, which recognizes a signal progression that is typical for a zero measurement or calibration measurement, for example a sudden pressure drop and/or a pressure drop that goes beyond a certain value, with subsequent constant pressure within predetermined limits.

Furthermore, a sensor device can be equipped with a switch button or some other manual switching device, which must be manually activated when a zero measurement (i.e. calibration measurement) is undertaken. As compared with an entry into the patient monitor, this has the advantage of significantly simplified handling, because, when a calibration measurement is undertaken, it is only necessary to handle the sensor device, not the sensor device and the patient monitor at the same time.

Generally, every variant of the invention described or indicated within the specification of the present application can be particularly advantageous, depending on the economic and technical conditions in an individual case. Unless something is stated to the contrary, or to the extent that this can generally be technically implemented, individual features of the embodiments described can be interchanged or combined with one another, as well as with features known per se from the prior art.

BRIEF DESCRIPTION OF THE DRAWINGS

In the following, examples of preferred embodiments of the present invention will be explained in greater detail, using the accompanying drawings.

The drawings are schematic, and, for reasons of a better illustration, not precise representations to scale. In particular, the relationships of the dimensions relative to one another can deviate from actual embodiments, even to a great extent.

Elements shown in both figures are provided with the same reference symbols in the respective individual figures. For reasons of a good overview, however, not all the elements that can also be seen in FIG. 2 have reference symbols in FIG. 1.

FIG. 1 shows two sensor devices according to the invention, in an arrangement together with a related patient monitor, a further sensor, as well as an additional blood pressure monitor connected to the further sensor.

FIG. 2 shows an enlarged, schematic representation of one of the sensor devices shown in FIG. 1.

DETAILED DESCRIPTION OF THE EMBODIMENTS

Figure 1:
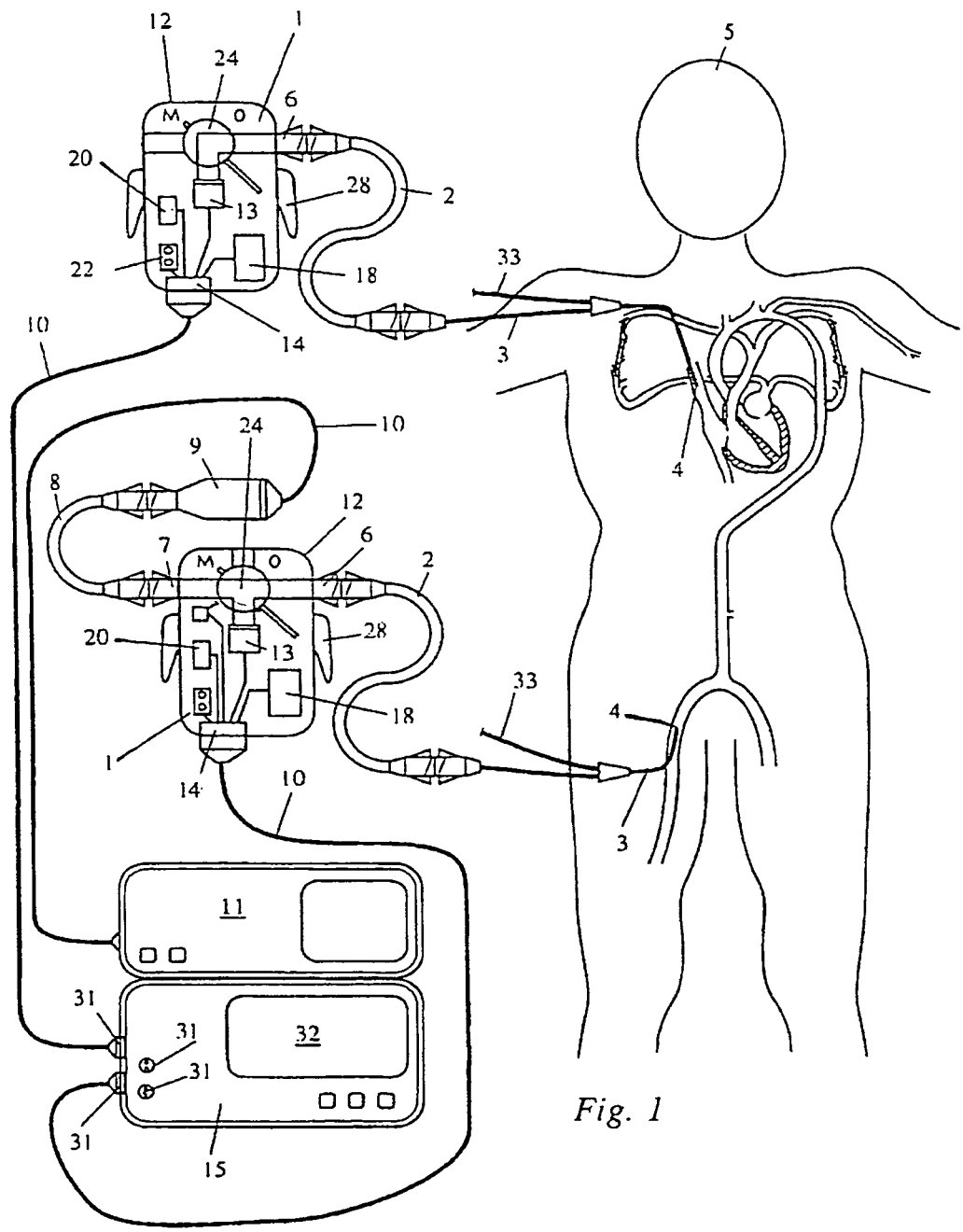
Figure 2:
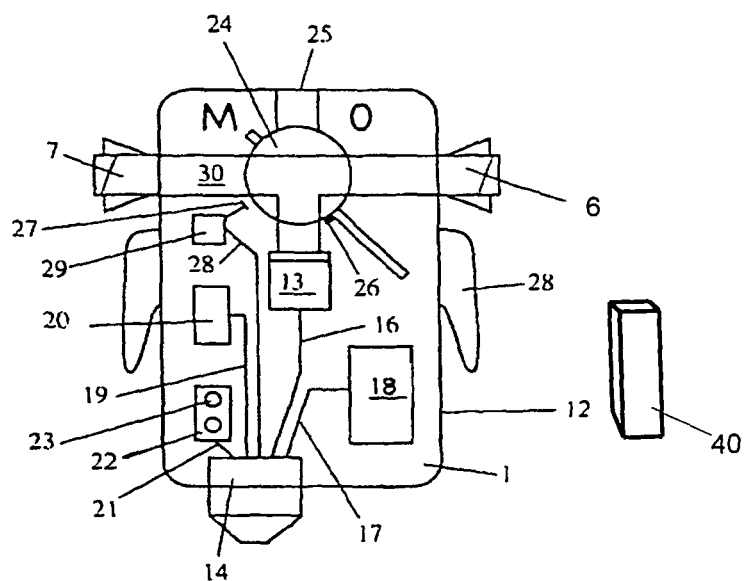

The portable sensor device 1 (the lower sensor device 1 shown in FIG. 1) is connected with the catheter 3 for measuring the arterial pressure at a measurement site 4 in the femoral artery of the patient 5, by way of a pressure hose 2. The pressure hose 2 is connected with the sensor device 1 by way of the measurement site interface 6, which is configured as a Luer lock connection. The electronic pressure sensor 13 is accommodated in the sensor housing 12 of the sensor device 1. The analog sensor signal of the pressure sensor 13 is output to the patient monitor 15 by way of a cable 10 connected with the patient monitor interface 14.

Aside from the channel 16 for the analog sensor signal, additional channels are provided for communication between sensor device 1 and patient monitor 15. A bidirectional channel 17 serves for writing to and querying the memory module 18, in which patient data can be stored. By way of the identification channel 19, an identification signal can be read out by the identification component 20. The identification signal is advantageously a sensor type identification, which allows the patient monitor 15 to recognize which type of sensor device 1 is involved. The identification signal can also be coded in forgery-proof manner (for example by means of encoding methods that are known per se), thereby making it possible to ensure that only suitable sensor devices 1 can be operated together with the patient monitor 15, in that the latter only accepts sensor signals from sensor devices 1 that make available a correctly coded identification signal. The operation of sensors that are not allowed, which could be hazardous to the patient, can be reliably avoided in this manner. An output device 22 having two light-emitting diodes 23 can be controlled by way of a further channel 21. In this way, warning signals of the patient monitor, for example if a physiological parameter being determined assumes a critical value, can be output close to the patient, for example by way of a red light-emitting diode 23. Another light-emitting diode, for example a green one, can indicate that the connection between patient monitor interface 14 and sensor interface of the patient monitor 15 is properly in effect, by way of the cable 10.

The sensor device 1 comprises a valve device 24, which can be used for calibrating the pressure sensor 13 against atmospheric pressure, in other words for zeroing. For this purpose, a calibration opening 25 is provided. The valve device 24 comprises a three-way cock having the settings "M" (measurement operation) and "0" (calibration measurement). The contactor 26 is brought into connection with the contact 27 in the setting "0". The switching contact produced in this manner is detected by the detector 29 (which measures capacitatively, for example), and a corresponding signal is transmitted to the patient monitor 15 by way of the channel 28. In this manner, zeroing of the sensor device 1 is automatically indicated to the patient monitor 15.

The sensor device 1 can be affixed, without tools, to a holder 40 such as a holder plate at the patient's bedside by means of the holder plate adapter 28 provided at the back of the sensor housing 12 and can be released from this plate again, preferably without tools.

A hydraulic connection 30 from the measurement site interface 6 to the additional, conventional pressure sensor 9, which is connected with the blood pressure monitor 11 by way of a cable 10, is established by way of the pressure line interface 7, also configured as a Luer lock connection, and a further pressure hose 8.

Furthermore, a second sensor device 1 (the upper device 1 shown in FIG. 1) according to the invention is connected with the patient monitor 15. The second portable sensor device 1 is connected with the venous catheter 3 for measuring the central venous pressure at a measurement site 4 in the vena cava superior of the patient 5, by way of a pressure hose 2. The pressure hose 2 is connected with the second sensor device 1 by way of the measurement site interface 1, which is configured as a Luer lock connection. The electronic pressure sensor 13 is accommodated in the sensor housing 12 of the second sensor device 1. The analog sensor signal of the pressure sensor 13 is output to the patient monitor 15 by way of a cable 10 connected to the patient monitor interface 14.

Just like the sensor device 1, the second sensor device 1 also has a memory module 18 in which patient data, calibration data, etc., can be stored, and an identification component 20, on which a sensor type identification is stored, which can be queried by the patient monitor 15, in order to recognize what type of second sensor device 1 is involved. Furthermore, again, an output device 22 that can be controlled by the patient monitor is provided. The sensor device 1 also has a set-on holder plate adapter 28 on its back side, by way of which it can be affixed, without tools, to a holder plate at the patient's bedside and released from it again, without tools.

The patient monitor 15 is equipped to evaluate the analog sensor signal of the pressure sensors 13. In this connection, it is unimportant with which of the connectors 31 of the sensor interface of the patient monitor 15 the respective sensor cables 10 are connected, because the patient monitor 15 recognizes, on the basis of the respective identification signal, from which sensor device 1 the sensor signal is coming, respectively.

The signal processing and evaluation in the patient monitor 15 can generally take place in such a manner as in the case of patient monitors known per se from the prior art. For example, the patient monitor can be programmed to perform common pulse contour algorithms. Furthermore, the patient monitor 15 can have further connectors 31 for connecting further sensors, and be equipped for evaluating further sensor signals. As is known per se from the prior art, the patient monitor 15 can thus be equipped for performing thermodilution methods (particularly transpulmonary ones), for processing plethysmography signals, for central venous oxygen saturation measurement, etc.

Physiological parameters determined from the sensor signals, such as cardiac output (Cardiac Output CO), cardiopulmonary volume compartments, etc., can be displayed graphically and numerically by way of the screen 32.

The catheters 3 can be equipped with one or more additional catheter ports 33, as they are known per se from the prior art, for the additional measurement tasks indicated.

What is claimed is:

1. A system for monitoring a patient comprising:
a portable sensor device and a separate patient monitor that is removably connected to the portable sensor device, the portable sensor device comprising the following:
an electronic pressure sensor configured to measure a physiological pressure at a measurement site of the body of the patient;
a measurement site interface configured to connect the electronic pressure sensor to a measurement site connector, wherein said measurement site connector is configured to establish a measurement connection between the electronic pressure sensor and the measurement site;
a patient monitor interface configured to connect the electronic pressure sensor to a patient monitor connector, wherein said patient monitor interface is configured to establish an analog signal connection between the electronic pressure sensor and the patient monitor for transmitting an analog sensor signal;
an optical and/or acoustical output device that is controllable directly by a data signal from the patient monitor;
an electronic identification device configured to make an identification signal available to the patient monitor, wherein the identification signal identifies a property of the analog sensor signal transmitted by the analog signal connection; and
a sensor housing configured to accommodate the electronic pressure sensor, the measurement site interface, the at least one electronic additional component, the electronic identification device, and the patient monitor interface, said sensor housing being separate from the patient monitor;
wherein the patient monitor interface further comprises an input channel for receiving the data signal from the patient monitor,
wherein the patient monitor interface further comprises a separate identification channel for output of the identification signal to the patient monitor, and
wherein the patient monitor is configured to evaluate the analog sensor signal and display a physiological parameter determined from the analog sensor signal on a display of the patient monitor.

2. The system according to claim 1, wherein the portable sensor device further comprises a memory configured to store patient data.

3. The system according to claim 1, wherein the measurement site interface is configured to connect a pressure-transferring hose element for establishing a hydraulic connection between the measurement site and the electronic pressure sensor.

4. The system according to claim 3, which further comprises a pressure line interface configured to connect the portable sensor device to a second sensor connector, wherein said second sensor connector is configured to produce a hydraulic connection between the pressure-transferring hose element and an additional sensor.

5. The system according to claim 1, wherein the portable sensor device is smaller than 100 millimeters in the direction of its greatest expanse.

6. The system according to claim 1, wherein the portable sensor device is lighter than 100 grams.

7. The system according to claim 1, wherein the portable sensor device is provided in a sterile packaging.

8. The system according to claim 1, wherein the sensor housing further comprises a mechanical holding connector.

9. The system according to claim 1, further comprising a valve device for calibrating configured to calibrate the electronic pressure sensor against atmospheric pressure,
  wherein the valve device is accommodated in the sensor housing,
  wherein the electronic identification device is equipped with a detector configured to recognize when the valve device calibrates the electronic pressure sensor against atmospheric pressure, and
  wherein the identification signal identifies the analog sensor signal as a zero signal when the detector recognizes the valve device is calibrated against atmospheric pressure.

* * * * *